United States Patent
Lu

(10) Patent No.: US 6,979,572 B1
(45) Date of Patent: Dec. 27, 2005

(54) COMPOSITIONS AND METHODS FOR INHIBITING INWARD-RECTIFIER POTASSIUM CHANNELS

(75) Inventor: Zhe Lu, Wynnewood, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/743,054

(22) PCT Filed: Jul. 7, 1999

(86) PCT No.: PCT/US99/15308

§ 371 (c)(1),
(2), (4) Date: Feb. 15, 2001

(87) PCT Pub. No.: WO00/01401

PCT Pub. Date: Jan. 13, 2000

Related U.S. Application Data

(60) Provisional application No. 60/092,033, filed on Jul. 7, 1998.

(51) Int. Cl.[7] .......................... A61K 38/00; C07K 14/00

(52) U.S. Cl. ............................ 436/501; 514/2; 514/13; 530/300; 530/326

(58) Field of Search ..................... 514/2, 13; 530/300, 530/326; 436/501

(56) References Cited

U.S. PATENT DOCUMENTS 3,878,297 A * 4/1975 Vick .......................... 424/539

OTHER PUBLICATIONS

Hider et al., Biochimica Biophysica Acta, vol. 667 (1981) pp. 197-208.*
Jin et al., Biochemistry vol. 38 (Oct. 8, 1999) pp. 14286-14293.*
Hider et al. Biochim. Et Biophys. Acta vol. 667 (1981) pp. 197-208.*
Habermann (1972) Science vol. 177 pp. 314-322.*
Biosequence Searching For The USPO@ (STN International, May 1996) pp. 30-31.*
Hider et al., "A comparative Stgructural Study of Apamin and Releated Bee Venom Peptides", *Biochemica Biophysica Acta*. 1981 667:197-208 [0006-3002].

* cited by examiner

*Primary Examiner*—Bennett Celsa
(74) *Attorney, Agent, or Firm*—Licata & Tyrrell P.C.

(57) ABSTRACT

The present invention provides compounds and methods of identifying and designing compounds which inhibit activity of inward-rectifier $K^+$ channels. In particular, compounds having a tertiapin-like α helix, such as a stable tertiapin derivative wherein the methionine residue in position 13 of tertiapin is replaced by glutamine, are described. Methods of using these compounds to control insulin secretion, and cardiac rhythm and electrical conduction, to modulate neurotransmissions of neurons, and to induce diuresis in mammals are also provided.

5 Claims, No Drawings

COMPOSITIONS AND METHODS FOR INHIBITING INWARD-RECTIFIER POTASSIUM CHANNELS

This application claims the benefit of U.S. Provisional Application Ser. No. 60/092,033, filed Jul. 7, 1998.

This invention was supported in part by funds from the U.S. government (NIH Grant No. CM55560 and NSF Grant No. IBN-9727436) and the U.S. government may therefore have certain rights in the invention.

FIELD OF THE INVENTION

This invention encompasses compositions and methods for inhibiting activity of inward-rectifier potassium channels such as G-protein-activated potassium channels and ROMK1 channels. G-protein-activated potassium channels mediate vagal control of heart rate as well as modulate neurotransmission in the nervous system. ROMK1 channels are critical for kidneys to maintain water and electrolyte balance. Blockade of these channels can lead to diuresis. A related inward-rectifier $K^+$ channel, ATP-sensitive $K^+$ channels, couple blood glucose levels to insulin secretion in pancreatic β cells. These channels are also believed to have an important pathophysiological role in cardiac ischemia. Compositions of the present invention are also expected to block these channels.

BACKGROUND OF THE INVENTION

Inward-rectifier $K^+$ channels function like $K^+$-selective diodes in the cell membrane. They pass much larger inward than outward $K^+$ current under symmetric ionic conditions. This unusual property is commonly referred to as inward rectification, which results from voltage dependent blockade by intracellular cations such as $Mg^{2+}$ and polyamines. Under physiological conditions, inward rectification manifests itself as a progressive reduction of the outward current, which allows the channel to control and regulate the resting membrane potential without impeding the generation of action potentials. Through regulation of the resting membrane potential inward-rectifier $K^+$ channels accomplish many important and diversified biological tasks. For example, the G-protein-gated $K^+$ channels control the heart rate and modulate neurotransmission; the ATP-sensitive $K^+$ channel couples blood glucose level to insulin secretion; the ROMK1 channel mediates water and electrolyte excretion in the kidney. The activity of most, if not all, inward-rectifier $K^+$ channels are regulated by intracellular signaling pathways such as G-proteins, inositol phosphates and protein kinases.

Inward-rectifier $K^+$ channels differ from voltage-activated $K^+$ channels not only in function but also in structure. Each of the four subunits of the inward-rectifier $K^+$ channels has only two transmembrane segments rather than six found in voltage-activated $K^+$ channels. The amino acid sequences between the two channel types are minimally conserved except for the signature sequence that forms the $K^+$ selective filter. Although most of the inward-rectifier $K^+$ channels are formed by four identical subunits, some channels are formed by non-identical subunits. An example of a non-identical subunit is the G-protein gated inward-rectifier $K^+$ channel (GIRK1/4) in the heart, which is formed by two different types of subunits, GIRK1 (GSK) and GIRK4 (CIR). In some cases, the channels are complexed with other proteins. For example, the ATP-sensitive $K^+$ channel is a complex of an inward-rectifier $K^+$ channel ($K_{ir}$ 6.2) and sulfonylurea receptor.

It has been well established that scorpion toxins inhibit the voltage- and $Ca^{2+}$-activated $K^+$ channels by blocking the ion conduction pore (MacKinnon, R. and Miller, C. J. Gen. Physiol. 1988 27:8491–8698; Miller, C. Neuron J. 1988 1:1003–1006; Park, C.-S. and Miller, C. Neuron 1992 9:307–313). Extensive mutagenesis studies have revealed much of the molecular interactions between the toxins and the channels. Recent crystallographic studies on a bacterial $K^+$ channel showed how the P-region makes up the outer part of the pore. The signature sequence forms the $K^+$-selective pore and the residues C-terminal to the signature sequence form the base of the external vestibule. The sequence N-terminal to P-region produces four turrets that surround the pore. When a scorpion toxin blocks the channel, it lies between two diagonally located turrets. The middle portion of the toxin contacts the vestibule base while the two ends contact the turrets. Because the channel is four-fold symmetric, a toxin molecule can bind to the channel in four equivalent orientations.

However, the pharmacology of inward-rectifier $K^+$ channels is not well developed. No high affinity ligands that directly target any inward-rectifier $K^+$ channels have been identified in the prior art. Out of the various scorpion toxins that target $K^+$ channels, only Lq2 and Δ-dendrotoxin block the ROMK1 inward-rectifier $K^+$ channel and the affinities are rather low ($K_d$=0.4 and 0.15 μM, respectively) (Lu, Z. and MacKinnon, R. Biochemistry 1997 36:6936–6940; Imredy et al. Biochemistry 1998 37:14867–14874).

Accordingly, there is a need for high affinity inhibitors against inward-rectifier $K^+$ channels.

Tertiapin is a small protein in honey bee venom which was initially purified over 20 years ago (Gauldie et al. Eur. Biochem. 61, 369–376). Because the venom was believed to contain materials beneficial to arthritis, many laboratories tried to identify the anti-arthritic components in the venom. This search led to the purification of many small proteins. Two of the purified small proteins, apamin and mast cell degranulating peptide (MCDP), were found to be inhibitors of voltage- and $Ca^{2+}$-activated $K^+$ channels (Blatz, A. L. and Magleby, K. L. Nature, 1986 323:718–720; and Stuhmer et al. EMBO J. 1989 8:3235–3244). However, tertiapin was one of the many other purified proteins without any clearly identified biological activity.

While the biological activity of tertiapin was unknown, the studies on tertiapin chemistry were quite advanced. The three-dimensional structure of tertiapin has been determined using NMR spectroscopy (Xu, X. and Nelson, J. W. Protein: Structure, Function and Genetics 1993 17:124–137). The structure shows that tertiapin is a highly compact molecule with a high density of positively charged residues. It consists of a type 4 reverse turn and an α-helix. A loop formed by an extended β sheet connects the turn and the helix. Four cysteines within the polypeptide chain form two disulfide bonds. The extensive interactions among the side-chains enhance the rigidity of the structure of tertiapin. The overall structure of tertiapin is very similar to that of apamin (Pease, J. H. and Wemmer, D. E. Biochemistry 1988 27:8491–8498). The main difference between these two structures is the relative position of the connecting loop and the α-helix. This difference is caused by the existence of an extra amino acid residue in the connecting loop of tertiapin.

Tertiapin has now been purified and identified as an inhibitor against two members of the inward-rectifier $K^+$ channel family. Both the GIRK1/4 and ROMK1 inward-rectifier $K^+$ channels are highly sensitive to tertiapin. Based upon homology, it is expected that ATP-sensitive $K^+$ channels will also be sensitive to tertiapin.

SUMMARY OF THE INVENTION

An object of the present invention is to provide a modified tertiapin peptide which comprises a stable tertiapin derivative wherein the methionine residue in position 13 of tertiapin is replaced by glutamine.

Another object of the present invention is to provide a method of inhibiting activity of inward-rectifier potassium channels such as G-protein-activated potassium channels, ROMK1 channels and related ATP-sensitive $K^+$ channels in an animal which comprises administering to an animal a compound comprising a tertiapin-like α helix.

Another object of the present invention is to provide methods of identifying compounds capable of inhibiting activity of inward-rectifier potassium channels such as G-protein-activated potassium channels, ROMK1 channels or related ATP-sensitive $K^+$ channels.

Yet another object of the present invention is to provide compositions and methods of using these compositions to control cardiac rhythm and electrical conduction, neuronal transmissions, and insulin secretion and to induce diuresis in mammals. These compositions comprise a compound having a tertiapin-like α helix.

DETAILED DESCRIPTION OF THE INVENTION

The small protein in honey bee venom, referred to as tertiapin, has now been identified as an inhibitor against two members of the inward-rectifier $K^+$ channel family. As demonstrated herein, both the GIRK1/4 and ROMK1 inward-rectifier $K^+$ channels are highly sensitive to tertiapin while the IRK1 inward-rectifier $K^+$ channel is relatively insensitive.

Venoms from various sources were screened for their activities against the inward-rectifier channel formed by GIRK1 (GSK) and GIRK4 (CIR) (Kubo et al. Nature 1993 362:127–132; Dascal et al. Proc. Natl. Acad. Sci. 1993 90:10235–10239; Krapvinsky et al. Nature 1995 374 135–141). The channel, GIRK1/4, is normally present in cardiac cells and is gated by muscarinic receptors through G-proteins. To study the GIRK1/4 channel, muscarinic receptors were co-expressed along with GIRK1/4 channel in *Xenopus oocytes*. Because oocytes have endogenous G-proteins, the channel can be activated by adding acetylcholine to the bath solution containing 100 mM $K^+$. The resting membrane potential of oocytes was held at 0 mV. To elicit the current through the channel, membrane voltage was briefly stepped to −80 mV and then to +80 mV. The current was recorded using a two-electrode voltage-clamp amplifier.

The activity in the venom was purified using reverse phase HPLC. The fraction containing the inhibitory activity was further purified by an additional HPLC step. The purity of the material was then examined on HPLC. Amino acid sequencing showed that the purified material consisted of twenty-one amino acid residues which included four cysteine and five basic residues (SEQ ID NO:1). The predicted and the observed mass of the purified material are 2460 and 2459 Daltons, respectively. The predicted and the observed amino acid composition of the material are also in good agreement. By searching the protein databases, it was determined that the amino acid sequence (SEQ ID NO:1) of the purified material is the same as that of tertiapin.

To demonstrate that tertiapin itself was the active inhibitory component, native tertiapin was compared with synthetic tertiapin. Chromatographic behaviors of the native and the synthetic tertiapin were indistinguishable. When injected separately, the native and the synthetic tertiapin had an identical retention time on the HPLC column. When co-injected, the native and synthetic tertiapin co-migrated on the column. Functionally, both the native and the synthetic tertiapin had almost identical inhibitory activity. The native and synthetic tertiapin, each at 10 nM, inhibited the GIRK1/4 current by about 50%. The fraction of unblocked currents in the presence of the native and synthetic tertiapin were plotted as a function of their concentrations. The equilibrium dissociation constants determined for the native and synthetic tertiapin were 8.2 nM and 8.6 nM, respectively.

Experiments were also performed to ascertain the specificity of tertiapin. The potential effects of apamin and MCDP, two other honey bee toxins known to inhibit voltage- and/or $Ca^{2+}$ activated $K^+$ channels and to share some homology with tertiapin, on the GIRK1/4 channel were examined. Both apamin and MCDP, at 1 μM concentration, inhibited the channel by only 20–30%. The affinities of the channel ($K_d$>1 μM) for these two toxins were at least 100-fold lower than that for tertiapin ($K_d$=8 nM). The effects of fifteen other toxins derived from various venoms were also examined. All of them had little or no effect.

The specificity of tertiapin was also examined in two other related inward-rectifier $K^+$ channels, ROMK1 and IRK1 (Kubo et al. Nature 1993 362:127–132; Kubo et al. Nature 1993 364:802–806). The ROMK1 channel was also very sensitive to tertiapin. In fact, the ROMK1 channel was even slightly more sensitive to tertiapin than the GIRK1/4 channel. The dissociation constant for tertiapin binding to the ROMK1 channel was 2.0 nM. In contrast, the IRK1 channel was relatively insensitive to tertiapin.

The effects of channel mutations on tertiapin affinity were then examined. Initial experiments focused on how mutations in the P-region of the ROMK1 channel affect the interaction of the channel with tertiapin. It was found that the affinity of the G127S channel for tertiapin was similar to that of the wild-type channel, whereas the affinities of N124A and F146A channels were much reduced. The equilibrium dissociation constants for the wild-type, N124A, G127S and F146A channels were 2.0 nM, 13.9 nM, 2.7 nM and 65.2 nM, respectively.

For a comparison, tertiapin inhibition of a mutant channel in which asparagine 171 in the second putative membrane-spanning segment (M2) was replaced with an aspartate was examined. The substitution of a negatively charged residue, aspartate, in the M2 segment is known to dramatically increase the channel affinity for intracellular cationic blockers such as $Mg^{2+}$ and polyamines (Lopatin et al. Nature 1994 372:366–369; Ficker et al. Science 1994 266:1068–1072; Fakler et al. Cell 1995 80:149–154, Lu, e and MacKinnon, R. Nature 1994 371:243–246; and Wible et al. Nature 1994 371:246–249). As a consequence, the N171D channel conducts much smaller outward $K^+$ current than the wild-type channel. Despite the dramatic effect of the N171D mutation on the binding of the intracellular cations to the channel, the mutation had little effect on the binding of extracellular tertiapin. The equilibrium dissociation constants of the wild-type and the mutant channels were 2.0 nM and 1.5 nM, respectively. Thus, these data are indicative of tertiapin inhibiting the channel by binding to the P-region.

Mutations at the residues that form the turrets (e.g., N124) and the vestibule base (e.g., F146 and F148) affected tertiapin binding to the ROMK1 inward-rectifier $K^+$ channel. The mutations around a glycosylation site, N117, in the P-region also affected tertiapin binding. Furthermore, the ROMK1 P-region mutations that weaken the binding of tertiapin are also known to weaken the binding of a scorpion toxin, Lq2. Thus, it is believed that a similar structure underlies both the scorpion toxin and the bee toxin receptors and that all $K^+$ channels have a similar $K^+$-selective pore despite a lack of conservation at most P-region residues (except the signature sequence) among various classes of K"channels.

However, contrary to what has been found for Lq2, a channel mutation, I142L, lowers the affinity of the ROMK1 channel for tertiapin by 8-fold. Residue 142 is located within the signature sequence that forms the K$^+$-selective part of the pore. The different effects of mutation I142L on the binding of the two toxins may be a consequence of tertiapin contacting the base of the vestibule more intimately than Lq2, which would also explain why tertiapin binds to the channel with a 200-fold higher affinity than Lq2.

Tertiapin is an asymmetric molecule, while the ROMK1 channel is likely four-fold symmetric because it is formed by four identical subunits (Ho et al. Nature 1993 362:127–132). The ROMK1 channel should have four identical binding orientations for tertiapin, similar to those for scorpion toxins on the voltage activated K$^+$ channels. The GIRK1/4 inward-rectifier K$^+$ channel is formed by two different types of subunits (GIRK1 and GIRK4) with a 2:2 stoichiometry (Silverman et al. J. Biol. Chem. 1996 271:30524–30528; Tucker et al. Am. J. Physiol. 1996 271:H379–H385). Thus, the GIRK1/4 channel likely does not contain four equivalent binding orientations for tertiapin. Study of the interaction of tertiapin with GIRK1/4 channel will be useful in determining the subunit arrangement, i.e. whether the two same subunits are located adjacently or diagonally, of this channel.

Tertiapin thus serves as useful tool for studying the physiology and the structure-function relationship of these channels. Knowledge of the structure of tertiapin makes it useful as a molecular probe to assess the distance between residues critical to binding of the molecule to the channel. These distances can then be used in the rational design of drugs targeted to these inward-rectifier K$^+$ channels. Based upon assessed distances between tertiapin residues determined to be critical for binding of tertiapin to the channel, other molecules with similar size with residues at similar distances can be synthesized and tested for their ability to bind to and inhibit these channels. Alternatively, tertiapin can be used as a template in the rational synthesis of new drugs targeted to inward-rectifier K+ channels. By "template" it is meant that tertiapin serves as a structural model for the design of compounds similar in shape and amino acid sequence and composition.

Tertiapin also serves as a powerful ligand for purifying functional channels as well as for screening pharmaceutical agents against these channels. Compounds which inhibit activity of inward-rectifier K$^+$ channels such as G-protein-activated potassium channels or ROMK1 channels can be identified by administering a test compound to an animal or cell culture system. In one embodiment of this assay, the level of activity of the channels in the animal or cell culture system is then measured and compared to the level of activity of the channels following administration of tertiapin to the animal or cell culture system. Test compounds which produce measured activity levels equal to or less than levels following administration of tertiapin are inhibitors of channel activity. Alternatively, in another embodiment, test compounds can be screened in high throughput competition assays wherein the ability of a test compound to compete with tertiapin for binding to the channel is determined in cell culture, purified channels or animals. In competition assays, it is preferred that tertiapin be detectably labeled for easy determination of displaced tertiapin in the cells, purified channels or animal. Those test compounds which displace tertiapin or bind more effectively to the channel can be determined by measuring unbound labeled tertiapin in the assay in the presence of the test compound. In a preferred embodiment, these assays are performed in cell culture systems. Examples of cell culture systems include, but are not limited to, native cells known to express the selected inward-rectifier K$^+$ channel and cells transfected with a heterologous gene to express the selected inward-rectifier K$^+$ channel. Test compounds identified as inhibitors are believed to be useful as pharmaceutical agents against the inward-rectifier K$^+$ channels such as G-protein-activated potassium channels or ROMK1 channels.

Instability of tertiapin can limit its utility in such screening assays. Methionine residue 13 in tertiapin interacts with residue F148 in the channel located just outside of the narrow region of the ROMK1 pore. However, this methionine residue in tertiapin is oxidized by air. This oxidation significantly hinders tertiapin binding to the channels. Accordingly, to overcome the oxidation problem, M13 in tertiapin was replaced with fourteen different non-oxidizable residues. These included A, D, E, F, G, I, L, N, Q, S, T, V, W and Y. For most of the tertiapin derivatives much higher concentrations were needed to inhibit half of the current through the ROMK1 channel. Out of these fourteen derivatives only the derivative in which M13 was replaced by glutamine binds to the channel with a K$_d$ value very similar to that of native tertiapin. This derivative is referred to herein as TPN$_Q$ and depicted as SEQ ID NO:2.

The specificity of tertiapin and TPN$_Q$ were compared among three inward-rectifier K$^+$ channels, GIRK1/4, ROMK1 and IRK1. Tertiapin and TPN$_Q$, at similar concentrations, inhibited about half of the currents through the GIRK1/4 or the ROMK1 channel. The IRK1 channel was insensitive to both tertiapin and TPN$_Q$ at a concentration of 2 $\mu$M. Thus, tertiapin and TPN$_Q$ have similar selectivity among the three inward-rectifier K$^+$ channels.

Mutations in the M1-M2 linker of the ROMK1 channel also affected TPN$_Q$ binding in similar fashion to tertiapin.

To identify all potential interaction residues in the M1-M2 linker and thus delineate the toxin receptor, the entire M1-M2 linker in the ROMK1 channel was alanine scanned. All the residues in the M1-M2 linker were replaced one at a time with alanine, or valine when the native residue is alanine (Clackson, T. and Wells, J. A. Science 1995 267: 383–386). Alanine has the smallest side-chain with the exception of glycine. Since glycine may introduce instability to a protein, an alanine substitution is generally used in an attempt to remove most side-chain interactions.

TPN$_Q$, at a concentration of 2 nM, inhibited a little more than half of the current through the ROMK1 channel. Alanine mutation at residues D116 and F146 dramatically reduced channel affinity for TPN$_Q$ manifested by eight- and fifty-fold higher concentrations of TPN$_Q$ being required to inhibit half of the current. Alanine mutation at P120 enhanced channel affinity for TPN$_Q$, seen as a fifteen-fold reduction in the concentration of TPN$_Q$ required to inhibit half of the current. Alanine mutations at some other channels residues, e.g., residues M128 and Q152, had little effect on channel affinity for TPN$_Q$.

The fraction of unblocked currents through the wild-type and five mutant channels were plotted against the concentration of TPN$_Q$. To determine the K$_i$ values for each channel, data were fitted with an equation that assumes the stoichiometry between the channel and TPN$_Q$ to be one-to-one. The analyses confirmed that mutant channels M128A and Q152A have affinities for TPN$_Q$ similar to that of the wild-type channel. The P120A channel has a fifteen-fold higher affinity, while the D116A and F146A channels have eight- and fifty-fold lower affinities for TPN$_Q$.

To summarize the effects of channel mutations on TPN$_Q$ binding, the ratios of K$_i$ values of the mutant channels and the wild-type channel were plotted in the natural logarithm form against the primary sequence of the M1-M2 linker. At many residue positions, e.g., between 131 and 145, no data were plotted since alanine mutations at these positions are lethal. Mutations at most residues between 114 and 123, as well as at residues 146 and 148, significantly affected the binding of $TPN_Q$.

As shown, $TPN_Q$ binds to the same receptor in the channel as tertiapin and has the same affinity and specificity as tertiapin. Due to its stability, however, $TPN_Q$ serves as an even more useful probe than tertiapin for studying the inward-rectifier $K^+$ channels and identifying pharmaceutical agents against these channels.

To identify the potential interaction residues in $TPN_Q$ and thus delineate its interaction surface, all the residues in $TPN_Q$ except for the four cysteine residues were alanine-scanned. Much higher concentrations of $TPN_Q$ derivatives with alanine at residues H12, K17 and K20 were required to inhibit half of the ROMK1 current. The alanine substitution at these three $TPN_Q$ residues affects the binding of $TPN_Q$ to the channel. Alanine mutation at residues L2 and I9 had almost no effect on the binding of $TPN_Q$ to the channel.

The fraction of unblocked ROMK1 currents by $TPN_Q$ and the five derivatives were plotted against their concentration. To determine the $K_i$ values of the channel for $TPN_Q$ and its derivatives, the data were fitted using an equation assuming a one-to-one stoichiometry between $TPN_Q$ and the channel. The analyses showed that the channel binds to $TPN_Q$ and its derivatives with alanine substitution at residues L2 and I9 with nearly identical $K_i$ values. However, when the channel binds to the tertiapin, derivatives with alanine substitution at residues H12, K17 and K20, the $K_i$ values were twenty-, five- and fifteen-fold lower, respectively.

Plotting of the ratios of $K_i$ values for channel binding to $TPN_Q$ derivatives and $TPN_Q$ itself (in a natural logarithm term) revealed that alanine mutation at the nine non-cysteine residues within the N-terminal half of the peptide had a minimum or modest effect on the channel-toxin interaction, whereas mutation at the eight non-cysteine residues within the C-terminal half generally had much more dramatic effects on the interaction.

Amidation occurs at the C-terminus of tertiapin as well as many other proteins purified from honey bee venom. Generally speaking, amidation in many proteins is critical for their biological activity. To examine whether the C-terminal amide in $TPN_Q$ plays a critical role in its interaction with the channel, the blocking activity of $TPN_Q$ with a C-terminal amide ($TPN_Q$-AM) versus a free carboxyl acid ($TPN_Q$-CA) was compared. It was found that the affinity of the channel for $TPN_Q$-AM is only about two-fold higher than that for $TPN_Q$-CA. Thus, the C-terminal amidation in $TPN_Q$ had only a very small effect on its binding to the ROMK1 channel.

The rate constant for $TPN_Q$ (and TPN) binding to the ROMK1 channel is rather large. Consequently, the rates of the channel inhibition by $TPN_Q$ at concentrations producing measurable channel inhibition were too fast to be accurately determined using the recording system described herein. However, a mutant channel, P120A, that binds to $TPN_Q$ with a fifteen-fold higher affinity ($K_i$=80 pM) than the wild-type channel was identified. The inhibition rates of this mutant channel by $TPN_Q$ at 20 to 500 pM were slow enough to be determined. In this concentration range, $TPN_Q$ inhibited 20 to 85% of the P120 channels.

The time course of current change upon washing-in and washing-out of $TPN_Q$ (200 pM) can be well fitted with single exponential functions. The reciprocals of the time constants for channel inhibition upon washing-in of $TPN_Q$ ($1/\tau_{on}$) and its recovery upon washing-out ($1/\tau_{off}$) were plotted against the concentration of $TPN_Q$. The plot showed that $1/\tau_{on}$ depends linearly on $TPN_Q$ concentration and $1/\tau_{off}$ is independent of the concentration. These findings indicate the existence of a one to one stoichiometry between $TPN_Q$ and the channel. In this case, $1/\tau_{on}=k_{on}[TPN_Q]+k_{off}$ and $1/\tau_{off}=k_{off}$, where $k_{on}$ and $k_{off}$ are the rate constants for tertiapin binding and unbinding, and $[TPN_Q]$ is the concentration of $TPN_Q$. From the slope of a linear fit of $1/\tau_{on}$ versus $[TPN_Q]$, a $k_{on}$ of approximately $3.0\times10^8$ $M^{-1}is^{-1}$ and from the averaged $1/\tau_{off}$, $k_{off}=0.024$ $s^{-1}$ were obtained. The $K_d$ value of 80 pM calculated from $k_{off}/k_{on}$, agrees with that determined from the equilibrium.

Thus, $TPN_Q$, an engineered non-air oxidizable derivative of tertiapin, inhibits the ROMK1 channel with nanomolar affinity. The value of the rate constant for $TPN_Q$ binding to the channel, $3.0\times10^8M^{-1}s^{-1}$, is unusually large for a protein—protein interaction. Since $TPN_Q$ has a high density of positively charged residues (four lysine, one arginine, one histidine and the carboxylamide), the large $TPN_Q$ binding constant is likely increased by some electrostatic interactions between the channel and the toxin. Similar large binding rate constants have been reported for the binding of a scorpion toxin (AgTx2) to a voltage-activated K' channel ($K_v$1.3) (Gross et al. Neuron 1994 13:961–966). However, results from the mutagenesis study on $TPN_Q$ indicate that the secondary structure makeup of its interaction surface is fundamentally different from those of scorpion toxins.

Charybdotoxin and other related scorpion toxins consist of a triple-stranded β sheet and an α helix (Bontems et al. Biochemistry 1992 31:7656–7764; Johnson, B. A. and Sugg, E. E. Biochemistry 1992 31:8151–8159; Johnson et al. Biochemistry 1994 33:15061–15070; Krezel et al. Protein Science 1995 4:1478–1489; and Renisio et al. Proteins: Structure, function and genetics 1999 34:417–426). The surface with which scorpion toxins binds to targeting channels, the interaction surface, is primarily formed by the residues in the β strands. Bee toxins, such as $TPN_Q$ also consist of an α helix formed by the C-terminal half of the peptide and some extended structures formed by the N-terminal half. Alanine mutations at the residues in the α helix dramatically impaired $TPN_Q$ binding, whereas those in the extended structures had minimal or modest effect. These results indicate that the interaction surface of $TPN_Q$ is primarily formed by the α helix rather than the extended structures as in scorpion toxins. Other bee toxins such as apamin and MCDP, which are structurally similar to tertiapin, comprise an α helix with an amino acid sequence and amino acid composition different from tertiapin. As described herein, these structurally similar toxins do not inhibit the activity of these inward-rectifier $K^+$ channels.

Many mutations in the M1-M2 linker of ROMK1 forming the external part of the ion conduction pore affect the interaction between the channel and $TPN_Q$. The pattern of the mutagenesis is indicative of $TPN_Q$ blocking the inward-rectifier $K^+$ channels by binding to the external vestibule of the $K^+$ pore.

From the results of mutagenesis studies on both ROMK1 and $TPN_Q$ together, it is believed that $TPN_Q$ and tertiapin block the $K^+$ pore by plugging its a helix into the vestibule of the $K^+$ pore while leaving its extended structural portion sticking out of the vestibule into the extracellular media. The extended structural portion provides a unique position for labeling of tertiapin or $TPN_Q$ which can in turn be used to tag the targeting channels. Further, identification of the α-helix being critical to blocking of the $K^+$ pore of these channels provides structural information important in selecting and designing other inhibitors of these channels. Based upon these experiments with $TPN_Q$ it is expected that test compounds having a tertiapin-like α helix will also be effective inhibitors of inward-rectifier $K^+$ channels. By "tertiapin-like α helix" it is meant a helix having a similar amino acid sequence and amino acid composition to P11 or H12 through K21 of tertiapin. Some variations to the amino acid sequence and/or composition between P11 through K21 of tertiapin are expected to result in compounds of similar activity.

G-protein-activated potassium channels mediate vagal control of heart rate as well as modulate neurotransmission among neurons in the nervous system. Thus, compounds identified as inhibitors of these channels are believed to be useful in mammals, including humans, in controlling cardiac rhythm and electrical conduction and in mediating neurological disorders characterized by hyperactivity of G-protein-activated channels in neurons of the nervous system.

ROMK1 channels are critical for maintenance of water and electrolyte balance by the kidneys. Blockade of ROMK1 channels leads to diuresis. Accordingly compounds identified as inhibitors of these channels will also be useful in mammals, including humans, to induce or promote diuresis.

Further, another related inward-rectifier channel, ATP-sensitive $K^+$ channels (Aguilar-Bryan, L. and Bryan, J. Endocr. Rev. 1999 20(2):101–35) couples blood glucose levels to insulin secretion. Thus, it is believed that tertiapin, $TPN_Q$ and compounds with tertiapin-like α helices, along with additional test compounds identified as inhibitors of channel activity will be useful in controlling insulin secretion in mammals, including humans suffering from diseases such as diabetes.

Compounds with a tertiapin-like a helix can thus be incorporated into a pharmaceutically acceptable vehicle and administered to a mammal to inhibit inward-rectifier $K^+$ channel activities. Pharmaceutically acceptable vehicles are well known in the art and can be selected routinely by those skilled in the art in accordance with the mode of administration. Effective amounts of the composition to be administered can also be determined routinely based upon inhibitory activity of the compound in vitro and/or in animal models.

The following nonlimiting examples are provided to further illustrate the present invention.

EXAMPLES

Example 1

Channel Expression

Oocytes harvested from *Xenopus laevis* frogs were digested with collagenase (2 mg/mL) in a solution containing: NaCl, 82.5 mM; KCl, 2.5 mM; $MgCl_2$, 1.0 mM; HEPES, 5.0 mM (pH 7.6) and were agitated on a platform shaker at a rate of 80 rpm for 90 minutes. The oocytes were then rinsed thoroughly with and stored in a solution containing: gentamicin, 50 μg/mL; NaCl, 96 mM; KCl, 2 mM; $CaCl_2$, 1.8 mM; MgCl, 1 mM; HEPES, 5 mM (pH 7.6). Defolliculated oocytes were selected at least 2 hours after the collagenase digestion. To express channels, the corresponding cRNA was directly injected into oocytes. To express the GIRK1/4 channel, GIRK1 and GIRK4 cRNAs were co-injected with either M2 or M4 receptor cRNA. All injections were carried out at least 16 hours after the collagenase treatment. The injected oocytes were stored in an 18° C. incubator.

Example 2

Channel Recording

All three inward-rectifier $K^+$ channels, GIRK1/4, ROMK1, and IRK1, were studied using a two-electrode voltage clamp amplifier (Oocyte Clamp OC-725C, Warner Instruments Corp.). The resistance of electrodes filled with 3 M KCl were 0.2–0.4 M Ω. To elicit current through the channel, the membrane potential of oocytes was stepped to −80 mV (100–125 ms) and then to +80 mV (100–125 ms) from the holding potential of 0 mV. Background leak currents were obtained by exposing oocytes to solutions containing tertiapin at concentrations greater than 100 fold of $K_d$. Tertiapin did not affect the currents in uninjected oocytes. The bath solution contained KCl, 100 mM; CaCl, 0.3 mM; $MgCl_2$, 1.0 mM; and HEPES, 10 mM (pH 7.6). To activate the GIRK1/4 channel, ACh (150 μM) was included in the bath solution. Tertiapin concentration was calculated using an extinction coefficient 6.1 $mM^{-1}$ $cm^{-1}$ at 280 nm wavelength. All toxin-containing solutions were freshly made by diluting stock solutions. Unless specified otherwise, tertiapin used in all experiments were made synthetically as described in Example 6. All other toxins were either recombinant toxins or purchased from Alomone Labs (Jerusalem, Israel).

Example 3

Molecular Biology

The GIRK1 and GIRK4 (CIR) cDNAs were cloned into pBluescript (SK−) plasmid (Stratagene) as described by Kubo et al. Nature 1993 364:802–806 and Krapivinsky et al. Nature 1995 374:135–141. The ROMK1 and IRK I cDNAs were cloned into pSPORT (Gibco-BRL) and pcDNA1/AMP (Invitrogen) plasmids as described by Ho et al. Nature 1993 362:127–132 and Kubo et al. Nature 1993 362:127–132. The M2 and M4 receptor cDNAs were cloned into pCTEM3 (Promega) plasmid. A mutation was introduced into the ROMK1 cDNA to create an NdeI site without altering the amino acid sequence. Mutations in the ROMK1 cDNA were produced using the polymerase chain reaction (PCR) primed with a mutagenic oligonucleotide. A sequenced 240 base pair fragment containing the mutation (between NdeI and BglII) was subcloned into a wild-type recipient version of the ROMK1 cDNA. The GIRK1, ROMK1, and IRK1 cDNAs were linearized using NotI. The GIRK4 cDNA was linearized using XhoI. The M2 and M4-receptor cDNAs were linearized using HindIII. All cRNAs, except for that of GIRK4, were synthesized using T7 polymerase (Promega). The GIRK4 cRNA was synthesized using T3 polymerase (Promega).

Example 4

Purification of Tertiapin

Lyophilized venom of honey bee (*Apis mellifera*) was dissolved in water at a concentration of 10 mg/ml. The venom suspension was first fractionated using a reverse phase HPLC (high performance liquid chromatograph) column (C18, 0.46×25 cm, 5 μm, 80 Å pore size, Beckman). The sample was eluted with a water and acetonitrile gradient. The active fraction was further purified with an additional step of reverse phase HPLC, in which the sample was eluted with a water and methanol gradient. The mass of the purified material was determined on a VG analytical MALDI-TOF spectrometer.

Example 5

Amino Acid Analysis and Sequence Determination

The amino acid analysis was done using a 420A derivatizer and a 103A separation system (Applied Biosystems). The extinction coefficient for tertiapin was calculated by determining the amino acid composition of an aliquot of tertiapin of known absorbance. The amino acid sequence of tertiapin was determined using 477A protein sequencer (Applied Biosystem) after derivatization of cysteine residues with 4-vinylpyridine.

Example 6

Synthesis, Mass Determination and Purification of Tertiapin and its Derivatives

Tertiapin and its derivatives were synthesized using a Rainin/Protein Technologies Symphony multi-peptide synthesizer and their mass was determined on a VG analytical MALDI-TOF Spectrometer. Synthetic tertiapin and all its derivatives have a C-terminal amide group. Tertiapin and its derivative spontaneously adopted the correct conformation in a solution containing 1 mM DTT and 10 mM Tris (pH 8.0) after DTT became oxidized. After folding into the correct conformation, they were purified using reverse phase HPLC.

The methionine residue (M13) in tertiapin may become oxidized spontaneously. Oxidation of M13 altered both the chromatographic behavior and the inhibitory activity of tertiapin. The oxidized form of tertiapin was eluted at a lower percentage of organic phase than the nonoxidized form. The oxidized form of tertiapin binds to the channel with lower affinity than the non-oxidized form. Therefore, tertiapin samples were examined daily using HPLC both before and after experiments. Only tertiapin samples containing less than 1% oxidized tertiapin, which was determined from the areas of absorbance peaks on HPLC, were used.

What is claimed is:

1. A modified tertiapin peptide comprising SEQ ID NO: 2.

2. A method of identifying compounds capable of inhibiting channel activity of inward-rectifier potassium channels comprising:
   (a) administering a test compound to an animal or cell culture system;
   (b) measuring channel activity of inward-rectifier potassium channels in the animal or cell culture system;
   (c) and comparing the measured channel activity with a level of channel activity of the inward-rectifier potassium channels following administration of tertiapin or modified tertiapin peptide of claim 1 to the animal or cell culture system, wherein a measured channel activity equal to or less than the levels of channel activity following administration of tertiapin or a modified tertiapin peptide of claim 1 is indicative of the test compound being an inhibitor.

3. A method of identifying compounds capable of inhibiting channel activity of inward-rectifier potassium channels comprising:
   (a) administering detectably labeled tertiapin or modified tertiapin peptide of claim 1 to a cell culture system, purified inward rectifier potassium channels or an animal;

SEQUENCE LISTING

<160> NUMBER OF SEQ ID NOS: 2

<210> SEQ ID NO 1
<211> LENGTH: 21
<212> TYPE: PRT
<213> ORGANISM: Apis mellifera

<400> SEQUENCE: 1

Ala Leu Cys Asn Cys Asn Arg Ile Ile Ile Pro His Met Cys Trp Lys
 1               5                  10                  15

Lys Cys Gly Lys Lys
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:synthetic

<400> SEQUENCE: 2

Ala Leu Cys Asn Cys Asn Arg Ile Ile Ile Pro His Gln Cys Trp Lys
 1               5                  10                  15

Lys Cys Gly Lys Lys
            20

(b) administering a test compound to the cell culture, purified inward-rectifier potassium channels or animal;

(c) and detecting unbound labeled tertiapin or the modified tertiapin peptide of claim 1 wherein the presence of unbound labeled tertiapin or the modified tertiapin peptide of claim 1 is indicative of the test compound being an inhibitor.

4. A pharmaceutical composition comprising a compound comprising amino acid residues 11 to 21 or 12 to 21 of SEQ ID NO:2 and a pharmaceutically acceptable vehicle.

5. The pharmaceutical composition of claim 4, wherein the compound comprises SEQ ID NO:2.

* * * * *